(12) United States Patent
Wheeler

(10) Patent No.: US 11,002,720 B2
(45) Date of Patent: May 11, 2021

(54) GAS ENERGY MEASUREMENT METHOD AND RELATED APPARATUS

(71) Applicant: Micro Motion, Inc., Boulder, CO (US)

(72) Inventor: Simon P. H. Wheeler, Erie, CO (US)

(73) Assignee: Micro Motion, Inc., Boulder, CO (US)

( * ) Notice: Subject to any disclaimer, the term of this patent is extended or adjusted under 35 U.S.C. 154(b) by 314 days.

(21) Appl. No.: 16/063,065

(22) PCT Filed: Jan. 27, 2016

(86) PCT No.: PCT/US2016/015160
§ 371 (c)(1),
(2) Date: Jun. 15, 2018

(87) PCT Pub. No.: WO2017/131670
PCT Pub. Date: Aug. 3, 2017

(65) Prior Publication Data
US 2019/0170723 A1    Jun. 6, 2019

(51) Int. Cl.
*G01N 33/22* (2006.01)
*G01N 9/00* (2006.01)
*G01N 9/36* (2006.01)

(52) U.S. Cl.
CPC ........... *G01N 33/225* (2013.01); *G01N 9/002* (2013.01); *G01N 9/36* (2013.01)

(58) Field of Classification Search
CPC ........ G01N 33/225; G01N 9/36; G01N 9/002; G01N 9/00
See application file for complete search history.

(56) References Cited

U.S. PATENT DOCUMENTS

| | | | |
|---|---|---|---|
| 2006/0151357 A1* | 7/2006 | Plopski | C10G 1/042 208/46 |
| 2013/0138361 A1 | 5/2013 | Wheeler | |
| 2014/0262836 A1* | 9/2014 | Liu | G01N 27/26 205/785.5 |
| 2016/0061114 A1* | 3/2016 | Guethe | F23N 5/242 60/776 |
| 2020/0041479 A1* | 2/2020 | Huber | G01N 33/225 |

OTHER PUBLICATIONS

"3098 Gas Specific Gravity Meter", Published by Micro Motion, Inc, 30985020 Rev. B, Published Oct. 2007 (Year: 2007).*

(Continued)

*Primary Examiner* — Herbert K Roberts
*Assistant Examiner* — John M Royston
(74) *Attorney, Agent, or Firm* — The Ollila Law Group LLC

(57) ABSTRACT

A method for determining an energy content of a hydrogen-rich gas mixture using a gas density meter (101) is provided. The method includes the steps of providing a vibratory gas density meter (101) and meter electronics (112) with the gas density meter (101). The meter electronics (112) communicate with at least one external input (116). The meter electronics (112) are configured to measure a density of the hydrogen-rich gas mixture, measure a specific gravity of the hydrogen-rich gas mixture, and derive a calorific value of the hydrogen-rich gas mixture using the derived specific gravity and a plurality of constant values.

20 Claims, 2 Drawing Sheets

(56) References Cited

OTHER PUBLICATIONS

J Agar et al: "The Use of Density Meters and Microprocessors for Energy Measurement and Control", First Industrial Energy Technology Conference, 1979, pp. 503-516, Houston, Texas, US, XP055260137, http://hdl.handle.net/1969.1/93842, Section "Energy Flow Rate Measurement Using Specific Gravity".
Product Data Sheet, PS-001484, Rev B, Jan. 2014 Micro Motion® Gas Specific Gravity Meters, © 2014 Micro Motion, Inc. All rights reserved.
Product Data Sheet, PS-001483, Rev C, Jan. 2014 Micro Motion® Gas Density Meters, © 2014 Micro Motion, Inc. All rights reserved.
Press release: Emerson releases next-generation meter for online gas specific gravity measurement, Boulder, Colorado. https://www.emerson.com/en-ca/news/automation/1310-specificgravity, (Oct. 2, 2013).

\* cited by examiner

GAS ENERGY MEASUREMENT METHOD AND RELATED APPARATUS

TECHNICAL FIELD

The present invention relates to gas energy measurements, and more particularly, to an improved vibratory meter and method for measuring gas energy.

BACKGROUND OF THE INVENTION

The usage and combustion of hydrogen rich gases such as fuel gas, tail gas, and bio-gas is heavily dependent upon the energy content of the gas itself. The energy content of a gas may be described as how much energy can be generated upon combustion. Energy, often measured in British thermal units (BTU), is thus a critical measurement for gas suppliers, transporters and users alike A BTU is defined as the amount of energy needed to cool or heat one pound of water by one degree Fahrenheit. Another commonly used parameter associated with the energy generated by the combustion of a gas (called calorific value or CV) is that of Wobbe Index (WI) or Wobbe number. This is an important parameter that indicates how easily a gas will burn, and not simply just how much energy can be generated by its combustion. The WI is employed because it is a reliable indicator of the interchangeability of fuel gases such as natural gas, liquefied petroleum gas (LPG), and other hydrocarbons, for example. The Wobbe index may be described by equation (1):

$$WI = \frac{CV}{\sqrt{SG}} \quad (1)$$

Where:
WI is the Wobbe Index;
CV is the calorific value; and
SG is the specific gravity.
The calorific value, CV, is often defined by equation (2):

$$CV = \frac{0.0235 + (0.00197 - [0.000329 \cdot M_{CO_2} + 0.000217 \cdot M_{N_2}])}{G_S} \quad (2)$$

Where:
$M_{CO_2}$=% $CO_2$ content; and
$M_{N_2}$=% $N_2$ content.
The Wobbe Index is often used to compare the combustion energy output of different composition fuel gases for a given application. For example, should fuels have identical Wobbe Indices, then for a given pressure and process settings on a particular apparatus, the energy output will be the same between the fuels. This is particularly important in processes or apparatuses where gases may be substituted for each other or where gas composition does not remain constant.

For hydrogen rich gases, there are two common types of instrumentation that are used to calculate/measure CV or WI—Gas Chromatographs (GC's) and Wobbe Index meters. GCs are relatively slow, as they separate gas into constituent components and then calculate gas parameters by separately analyzing the properties of the individual mixture gases. Wobbe Index meters typically combust a gas to measure the energy or calculate CV or WI. However, for non-combustion Wobbe Index meters, a major problem in obtaining accurate measurements relates to the accounting for the percent of inert gases and percentage of Hydrogen ($H_2$) present in the gas mixture. Inert gases drastically change the energy content generated by the overall mixture—as does Hydrogen. The inert gases most often encountered in hydrogen-rich gas mixtures and fuel gases are Carbon Dioxide ($CO_2$), Carbon Monoxide (CO), and Nitrogen ($N_2$). Of these, $CO_2$ and CO are relatively easy to measure, as near infra-red (NIR) monitors are available for this purpose. Nitrogen measurements, however, remain cumbersome to measure, and typically require a GC.

When it comes to measuring hydrogen content, a number of thermal conductivity analyzers are available that can directly output this variable, so measurement of this parameter is relatively simple. In most Hydrogen-rich and fuel gas mixtures, Nitrogen content is a relatively small percentage of the mixture, and generally relatively constant. Therefore, a constant value of $N_2$ may often be employed in the determination of accurate energy measurement values. For CO, $CO_2$ and $H_2$, this is definitely not the case. Wild swings in concentration of these components is typical, often occurring over a period of mere seconds. This is a primary reason that GC technology fails to meet the market need for fast response gas energy and Wobbe Index (WI) measurement.

Gas Chromatographs are widely used in the gas measurement industry, and while they provide an accurate output of the full gas composition of the gas mixture under measurement, they have a number of significant limitations. First, GCs exhibit an extremely high cost of ownership. Systems and parts are expensive to buy, and a number of moving parts require significant and frequent servicing. Second, GCs require regular calibration. Third, the calibration gases needed for the calibration process must be generated, which is timely and expensive. Fourth, skilled and trained operators are required for GC operation, which increases operating costs. Fifth, the response time is typically extremely slow, with outputs typically updated about every 7 minutes.

As noted above, Wobbe Index meters or calorimeters can be used for fuel gas or $H_2$ rich gas mixtures, yet they also exhibit a number of limitations. First, there is a high cost of purchase and ownership. Second, due to the combustion often needed for measurements, such units must often be installed in non-hazardous areas. Third, these meters also require extensive utilities, such as high current electrical inputs and compressed air-gas bottle supplies. They are therefore expensive to install and operate. Along these lines, the waste gas exhausted by these units is typically around the order 800° C., which is potentially dangerous and expensive to mitigate in hazardous environments, such as those found in oil refineries, for example.

An alternative method and apparatus for calculating CV, WI, density, base density, SG, etc. is needed. A method and apparatus for these calculations that updates quickly is needed. Additionally, a method and apparatus is needed that minimizes safety risks. A non-combustive, fast-response method and apparatus is provided to address these and other issues, and an advance in the art is achieved. Embodiments disclosed provide an alternative method to determine gas energy and WI in a hydrogen-rich gas mixture. This method and apparatus is especially well-suited for a gas composition that is not known and/or where existing standards that relate gas specific gravity to energy content are not applicable.

SUMMARY OF THE INVENTION

A method is provided for determining an energy content of a hydrogen-rich gas mixture using a gas density meter according to an embodiment. The method comprises the steps of providing a vibratory gas density meter and a meter electronics with the gas density meter configured to communicate with at least one external input. The method additionally comprises the steps of measuring a density of the hydrogen-rich gas mixture, deriving a specific gravity of the hydrogen-rich gas mixture, and deriving a calorific value of the hydrogen-rich gas mixture using the derived specific gravity and a plurality of constants and/or variables.

A system is provided for measuring gas energy according to an embodiment. The system comprises a vibratory gas density meter configured to calculate a specific gravity of a hydrogen-rich gas mixture. The system additionally comprises a communication line configured to connect to an external input and meter electronics for operating the vibratory gas density meter that is in communication with the communication line. The meter electronics is configured to measure a density of the hydrogen-rich gas mixture and derive a calorific value of the hydrogen-rich gas mixture using the measured specific gravity and a plurality of constants and/or variables.

Aspects

According to an aspect, a method for determining an energy content of a hydrogen-rich gas mixture using a gas density meter comprises: providing a vibratory gas density meter; providing meter electronics with the gas density meter configured to communicate with at least one external input; measuring a density of the hydrogen-rich gas mixture; measuring a specific gravity of the hydrogen-rich gas mixture; and deriving a calorific value of the hydrogen-rich gas mixture using the measured specific gravity and a plurality of constant values.

Preferably, a Wobbe Index value of the hydrogen-rich gas mixture is calculated.

Preferably, the calorific value (CV) is calculated according to an equation comprising: $CV = A + (B \cdot \text{percent } H_2) + (C \cdot \text{percent } CO) + (D \cdot \text{percent } CO_2) + (E \cdot \text{percent } N_2) + (F \cdot SG)$, where A-F comprise the constant values, and SG comprises the specific gravity.

Preferably, A is between about 144.8 and 150.8, wherein B is between about −2.5 and −2.6, wherein C is between about −12.15 and −12.65, wherein D is between about −47.7 and −49.65, wherein E is between about −24.68 and −25.69, and wherein F is between about 1528.7 and 1591.1.

Preferably, A is about 147.8458, B is about −2.55807, C is about −12.3963, D is about −48.685065, E is about −25.18546, and F is about 1559.94255.

Preferably, the external input comprises a percent $H_2$ value of the hydrogen-rich gas mixture.

Preferably, the percent $H_2$ value is determined with a thermal conductivity meter.

Preferably, the external input comprises a percent CO value of the hydrogen-rich gas mixture.

Preferably, the percent CO value is determined with a near infrared meter.

Preferably, the external input comprises a percent $CO_2$ value of the hydrogen-rich gas mixture.

Preferably, the percent $CO_2$ value is determined with a near infrared meter.

Preferably, the external input comprises a percent $N_2$ value of the hydrogen-rich gas mixture.

Preferably, the percent $N_2$ value is determined with a gas chromatograph.

Preferably, deriving the calorific value is accomplished in a frequency of under about 10 seconds.

According to an aspect, a system for measuring gas energy comprises: a vibratory gas density meter configured to calculate a specific gravity of a hydrogen-rich gas mixture; a communication line configured to connect to an external input; meter electronics for operating the vibratory gas density meter in communication with the communication line, wherein the meter electronics is configured to measure a density of the hydrogen-rich gas mixture and derive a calorific value of the hydrogen-rich gas mixture using the derived specific gravity and a plurality of constant values.

Preferably, the external input comprises at least one of a near infrared meter, a thermal conductivity meter, and a gas chromatograph.

Preferably, the meter electronics is configured to calculate a Wobbe Index value of the hydrogen-rich gas mixture.

Preferably, the calorific value (CV) is calculated according to an equation comprising: $CV = A + (B \cdot \text{percent } H_2) + (C \cdot \text{percent } CO) + (D \cdot \text{percent } CO_2) + (E \cdot \text{percent } N_2) + (F \cdot SG)$, where A-F comprise the constant values, and SG comprises the specific gravity.

Preferably, A is between about 144.8 and 150.8, wherein B is between about −2.5 and −2.6, wherein C is between about −12.15 and −12.65, wherein D is between about −47.7 and −49.65, wherein E is between about −24.68 and −25.69, and wherein F is between about 1528.7 and 1591.1.

Preferably, A is about 147.8458, B is about −2.55807, C is about −12.3963, D is about −48.685065, E is about −25.18546, and F is about 1559.94255.

Preferably, at least one of the percent H2, percent CO, percent $CO_2$, and percent N2 is provided to the meter electronics from the external input.

BRIEF DESCRIPTION OF THE DRAWINGS

The same reference number represents the same element on all drawings. The drawings are not necessarily to scale.

DETAILED DESCRIPTION OF THE INVENTION

Figure 1:
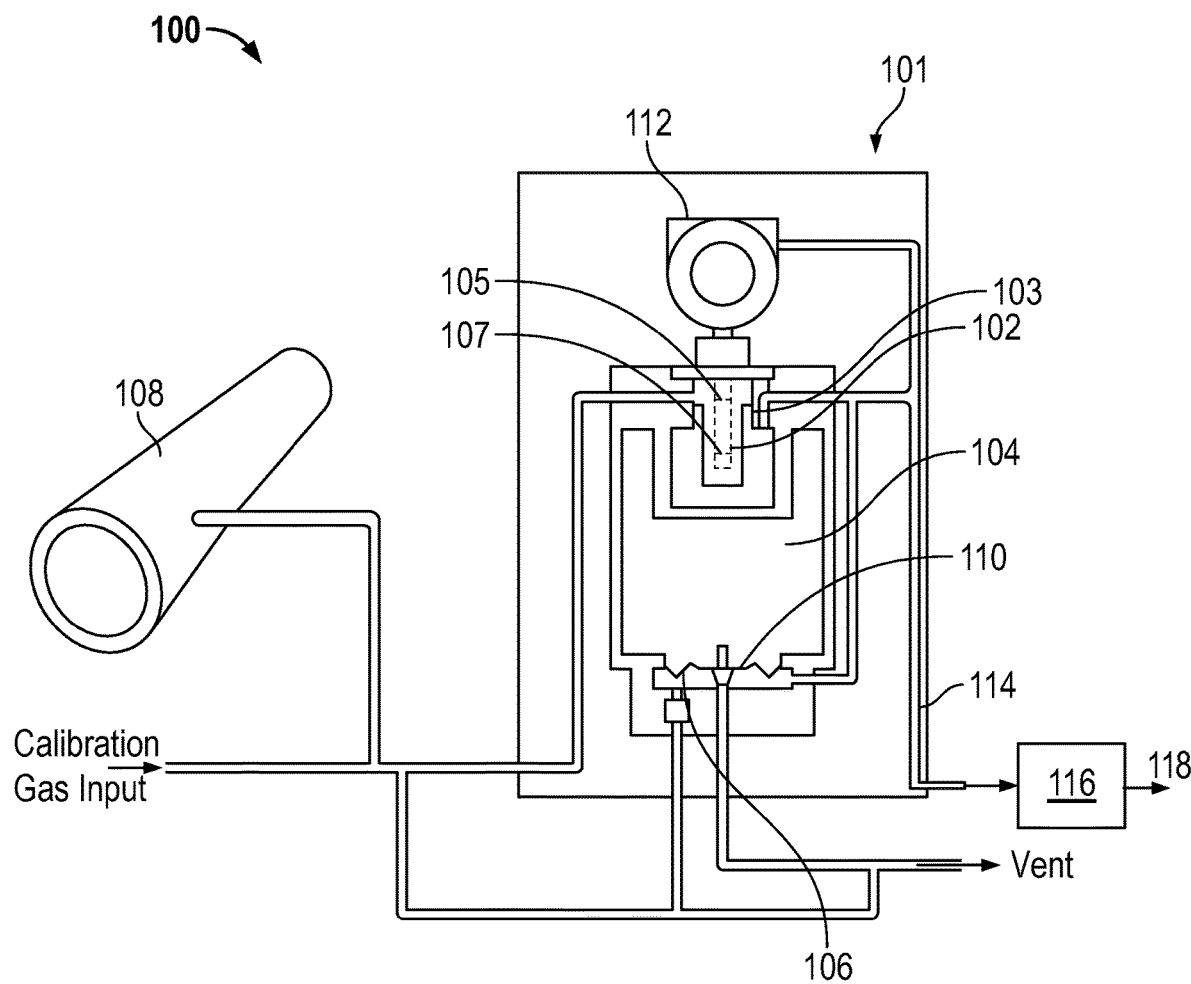
FIG. 1 illustrates a system for measuring gas energy according to an embodiment.
Figure 2:
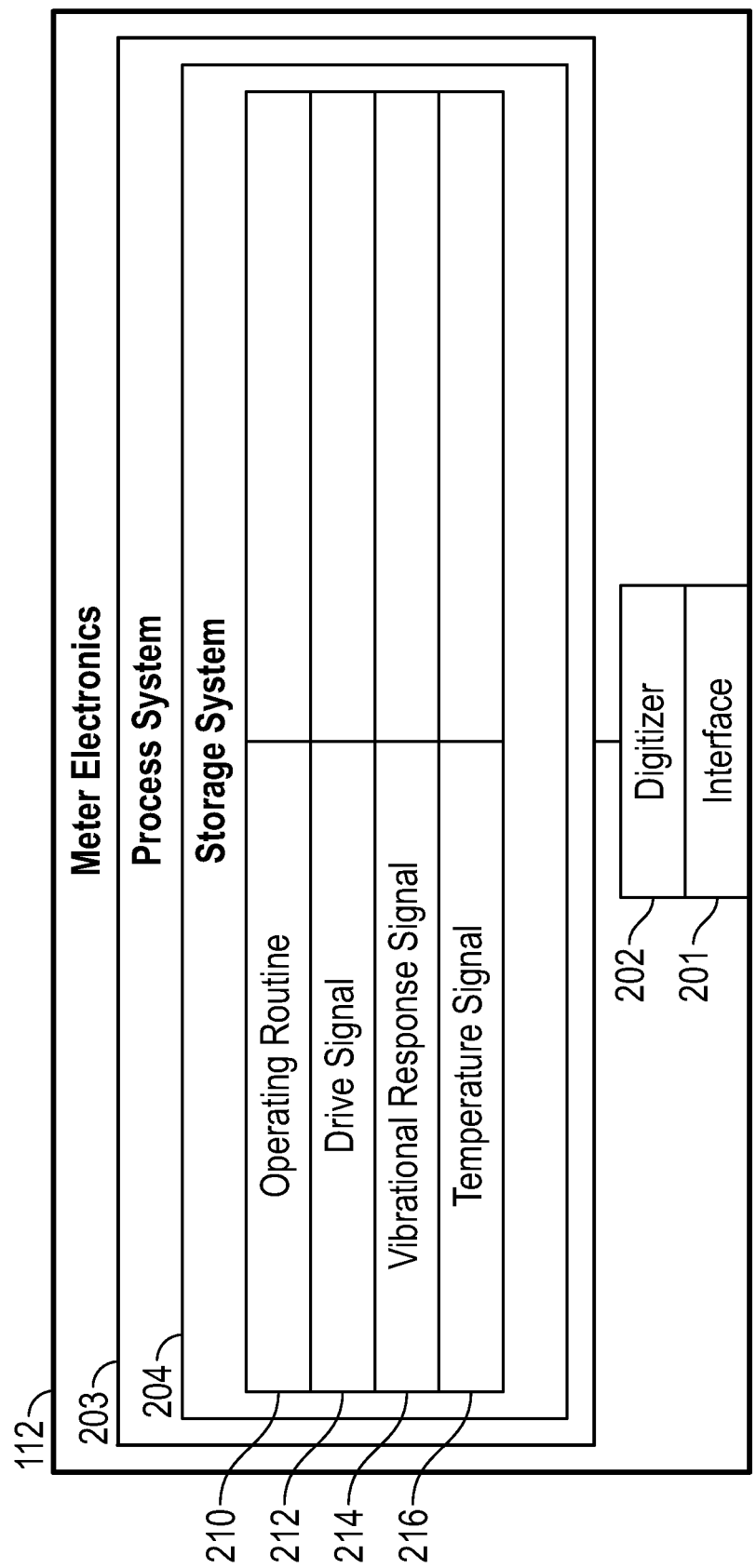
FIG. 2 illustrates meter electronics according to an embodiment.

FIGS. 1, 2, and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

FIG. 1 illustrates a system 100 for measuring gas energy according to an embodiment. A density meter 101 is provided to measure the specific gravity of a gas. To measure the specific gravity of a gas, the density meter 101 utilizes a resonating element 102 surrounded by a constant volume reference chamber 104 filled with a fixed quantity of gas. A separator diaphragm 106 inside the reference chamber ensures that the pressure of a sample gas, delivered by gas line 108, in the density meter 101 is equal to that of the reference gas by controlling a pressure control valve 110.

The density meter's 101 resonating element 102 is located at least partially within a housing 103. The housing 103 or the resonating element 102 may include flanges or other members for operatively coupling the density meter to a pipeline or similar gas delivering device in a gas-tight manner. Often, the resonating element 102 is cantilever mounted to the housing at one end of the housing, with the opposite end of the resonating element 102 free to vibrate. The resonating element 102 may, in an embodiment, define a plurality of gas apertures that allow gas to enter the density meter and flow between the housing and the resonating element 102. Therefore, the gas contacts the inside as well as the outside surfaces of the resonating element 102. This allows a greater surface area of the resonating element 102 to be exposed to gas, and therefore provide more accurate measurements. In other examples, apertures may be provided in the housing, and apertures in the resonating element 102 may not be required.

The resonating element 102 may be vibrated at or near to a natural (i.e., resonant) frequency. By measuring a resonant frequency of the member in a presence of a gas, the density of the gas may be determined.

A driver 105 and a vibration sensor 107 are typically positioned on a spool body positioned proximate the resonating element 102. The driver 105 receives a drive signal from a meter electronics 112 and vibrates the resonating element 102 at or near a resonant frequency. The vibration sensor 107 detects the vibration of the resonating element 102 and sends the vibration information to the meter electronics 112 for processing. The meter electronics 112 determines the resonant frequency of the resonating element 102 in combination with the gas under test, and generates a density measurement from the measured resonant frequency.

The specific gravity of a gas is the ratio of its molecular weight (M) to the molecular weight of standard dry air. In an embodiment, the density meter 101 yields a frequency output that is proportional to the gas specific gravity, and may also generate a gas molecular weight (M).

The most relevant parameters when measuring hydrogen-rich or fuel gases are:
a. specific gravity (SG)
b. temperature (T)
c. pressure (P)
d. molecular weight (M)
e. Percent inert gas (e.g. % N, % $CO_2$)
f. Calorific value/BTU (CV)
g. Wobbe Index (WI)
h. relative density ($\rho_{rel}$)

An embodiment of the system 100 provides measurement and/or calculation of at least one of the parameters above, without the need for combusting a gas or relying on a GC. In an embodiment, the density meter 101 is calibrated to output SG—using the molecular weight of a plurality of calibrations gases. For example, without limitation, three calibration gases as the low, medium and high range points are contemplated. Calibrations with more or less than three gases is also contemplated.

In an embodiment, the system accepts at least one external input 116. The external input 116 may comprise measurements of, inter alia, percent $CO_2$, percent CO, percent $H_2$, and percent $N_2$. This data is provided to meter electronics 112 via a communication line 114. In conjunction with separate external inputs 116 from analyzers such as, for example without limitation, thermal conductivity meters (that provide real time percent $H_2$ value), near infrared (NIR) meters (that provide real time percent CO and/or percent $CO_2$ values), and gas chromatographs (that provide percent $N_2$ values), the system 100 may produce an extremely accurate measurement of calorific value, BTU and Wobbe Index, and may effectively do so in roughly real-time. By providing a multi-meter/multi-technology approach, the system 100 produces an inherently fast response, yet does not require a known full composition of the gas being measured. Additionally, the need for gas combustion is obviated, which is otherwise the typical approach employed by calorimeters and Wobbe Index meters.

This multi-technology input embodiment relies upon an accurate fast response measurement of specific gravity that the density meter 101 provides. An embodiment has been derived by analyzing over 30 different hydrogen gas and fuel gas mixtures—all of which are outside the scope of standards where specific gravity is directly related to the energy content of the gas, such as the AGA5 standard, for example without limitation. The relationship below between energy content, specific gravity and percent $N_2$, percent CO, percent $CO_2$, and percent $H_2$ is derived according to an embodiment, as described by equation (3):

$$CV = A + (B \cdot \% \ H_2) + (C \cdot \% \ CO) + (D \cdot \% \ CO_2) + (E \cdot \% \ N_2) + (F \cdot SG) \quad (3)$$

Where A-F are constants:
A=147.8458
B=−2.55807
C=−12.3963
D=−48.685065
E=−25.18546
F=1559.94255

Note that from the above coefficients, the greatest sensitivity to measurement is that of SG, hence an accurate measurement of SG, derived from the density meter 101 is critical. Using this equation, typical measurement errors are less than ±0.25%, with maximum observed deviations less than ±0.9%. It should be noted that constants A-F may be altered by as much as ±5%.

In an embodiment, once CV is determined, the Wobbe Index is calculated according to equation (1). It should be noted that other calculations to determine CV are also contemplated.

It will be appreciated by those skilled in the art that various modifications of that which is described above is possible without departing from the scope of the invention. By way of example only, constant A in equation (3) above could be trimmed or refined from time to time by separately measuring % CO using a sampling technique (e.g. NIR) and using that measurement to refine the calculation made according to a far more rapid time scale inherent in the claimed method.

FIG. 2 illustrates meter electronics 112 for the density meter 101 according to an embodiment. The meter electronics 112 may include an interface 201 and a processing system 203. The interface 201 transmits a drive signal to the resonating element 102. The meter electronics 112 receives and processes at least one sensor signal from a sensor, such as a vibration sensor 107 signal, that measures oscillations associated with the resonating element 102.

The interface 201 can perform any necessary or desired signal conditioning, such as any manner of formatting, amplification, buffering, etc. Alternatively, some or all of the signal conditioning can be performed in the processing system 203.

In addition, the interface 201 can enable communications between the meter electronics 112 and external devices, such as via the communication link 114, for example. The interface 201 can transfer measurement data to external devices via a communication link 118 and can receive commands, updates, data, and other information from external devices and external gas measurement apparatuses. The interface 201 and communication link 114 may be capable of any manner of electronic, optical, or wireless communication.

The interface 201 in one embodiment comprises a digitizer, wherein sensor signals comprise analog sensor signals. The digitizer samples and digitizes the analog sensor signals and produces corresponding digital sensor signals. The interface/digitizer can also perform any needed decimation, wherein the digital sensor signal is decimated in order to reduce the amount of signal processing needed and to reduce the processing time.

The processing system 203 conducts operations of the meter electronics 112 and processes gas measurements from the density meter 101. The processing system 203 executes an operating routine 210 and processes the density measurements in order to produce one or more density characteristics (or other density measurements). The processing routine comprises, inter alia, routines for determining gas specific gravity, gas density, gas temperature, gas pressure, gas molecular weight, percent inert gas, calorific value, and Wobbe Index.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204. The storage system 204 may be coupled to the processing system 203 or may be integrated into the processing system 203.

The storage system 204 can store information used for operating the density meter 101, including information generated during the operation of the density meter 101. The storage system 204 can store one or more signals that are used for vibrating the resonating element 102, and that are provided to a driver 105 for actuating the resonating element 102, such as a drive signal 212. In addition, the storage system 204 can store vibrational response signals 214 generated by a vibration sensor 107 as a result of the resonating element 102. Temperature signals 216 may also be utilized by meter electronics and related algorithms.

It will thus be appreciated that the embodiments utilize a density meter 101 in combination with commercially available gas meters to provide fast and accurate measurements of both Calorific Value and Wobbe Index. The embodiments described above provide Calorific Value and/or Wobbe Index measurements at a frequency of about every 5-10 seconds as opposed to the typical response time of around 7 minutes when using a gas chromatograph. In other embodiments, the frequency is greater or less than every 5-10 seconds. This fast response time optimizes combustion efficiency for combustion-requiring operations, and concomitantly minimizes NOx & SOx emissions, as well as related taxation. Embodiments also yield a stable steam heat supply for certain applications. Thus the present invention could be used in gas blending applications and is ideal for custody transfer applications. Since over 50% of a refinery's (or manufacturing plant's) operating costs is typically due to energy (i.e. steam) production, the present embodiments may lower operating costs in such applications. These benefits are realized, while eliminating safety risks inherent in incendive technologies.

The detailed descriptions of the above embodiments are not exhaustive descriptions of all embodiments contemplated by the inventor to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. A method for determining an energy content of a hydrogen-rich gas mixture using a gas density meter, comprising the steps of:
providing a vibratory gas density meter;
providing meter electronics with the gas density meter configured to communicate with at least one external input, wherein the external input comprises a percent $H_2$ value of the hydrogen-rich gas mixture;
measuring a density of the hydrogen-rich gas mixture;
measuring a specific gravity of the hydrogen-rich gas mixture; and
deriving, using the meter electronics of the gas density meter, a calorific value of the hydrogen-rich gas mixture using the measured specific gravity, the external input, and a plurality of constant values.

2. The method of claim 1, wherein a Wobbe Index value of the hydrogen-rich gas mixture is calculated.

3. The method of claim 1, wherein the calorific value (CV) is calculated according to an equation comprising: $CV = A + (B \cdot \text{percent } H_2) + (C \cdot \text{percent } CO) + (D \cdot \text{percent } CO_2) + (E \cdot \text{percent } N_2) + (F \cdot SG)$, where A-F comprise the constant values, and SG comprises the specific gravity.

4. The method of claim 3, wherein A is between 144.8 and 150.8, wherein B is between −2.5 and −2.6, wherein C is between −12.15 and −12.65, wherein D is between −47.7 and −49.65, wherein E is between −24.68 and −25.69, and wherein F is between 1528.7 and 1591.1.

5. The method of claim 3, wherein A is about 147.8458, B is about −2.55807, C is about −12.3963, D is about −48.685065, E is about −25.18546, and F is about 1559.94255.

6. The method of claim 1, wherein the percent $H_2$ value is determined with a thermal conductivity meter.

7. The method of claim 3, wherein the external input comprises a percent CO value of the hydrogen-rich gas mixture.

8. The method of claim 7, wherein the percent CO value is determined with a near infrared meter.

9. The method of claim 3, wherein the external input comprises a percent $CO_2$ value of the hydrogen-rich gas mixture.

10. The method of claim 9, wherein the percent $CO_2$ value is determined with a near infrared meter.

11. The method of claim 3, wherein the external input comprises a percent $N_2$ value of the hydrogen-rich gas mixture.

12. The method of claim 11, wherein the percent $N_2$ value is determined with a gas chromatograph.

13. The method of claim 1, wherein deriving the calorific value is accomplished in a time of under 10 seconds.

14. A system (100) for measuring gas energy, comprising:
a vibratory gas density meter (101) configured to calculate a specific gravity of a hydrogen-rich gas mixture;
a communication line (114) configured to connect to an external input (116), the external input comprising a percent $H_2$ value of the hydrogen-rich gas mixture;
meter electronics (112) for operating the vibratory gas density meter (101) in communication with the communication line (114), wherein the meter electronics (112) is configured to measure a density of the hydrogen-rich gas mixture and derive, using the meter electronics of the gas density meter, a calorific value of the hydrogen-rich gas mixture using the derived specific gravity, the external input, and a plurality of constant values.

15. The system (100) of claim 14, wherein the external input (116) comprises at least one of a near infrared meter, a thermal conductivity meter, and a gas chromatograph.

16. The system (100) of claim 14, wherein meter electronics (112) is configured to calculate a Wobbe Index value of the hydrogen-rich gas mixture.

17. The system (100) of claim 14, wherein the calorific value (CV) is calculated according to an equation comprising: $CV = A + (B \cdot \text{percent } H_2) + (C \cdot \text{percent } CO) + (D \cdot \text{percent } CO_2) + (E \cdot \text{percent } N_2) + (F \cdot SG)$, where A-F comprise the constant values, and SG comprises the specific gravity.

18. The system (100) of claim 17, wherein A is between 144.8 and 150.8, wherein B is between −2.5 and −2.6, wherein C is between −12.15 and −12.65, wherein D is between −47.7 and −49.65, wherein E is between −24.68 and −25.69, and wherein F is between 1528.7 and 1591.1.

19. The system (100) of claim 17, wherein A is about 147.8458, B is about −2.55807, C is about −12.3963, D is about −48.685065, E is about −25.18546, and F is about 1559.94255.

20. The system (100) of claim 17, wherein at least one of the percent CO, percent $CO_2$, and percent $N_2$ is provided to the meter electronics (112) from the external input (116).

\* \* \* \* \*